United States Patent
Raja et al.

(10) Patent No.: US 9,650,404 B2
(45) Date of Patent: May 16, 2017

(54) CURCUMIN DERIVATIVES

(75) Inventors: Krishnaswami Raja, Staten Island, NY (US); Alejandra Alonso, Staten Island, NY (US); Probal Banerjee, Staten Island, NY (US); Sukanta Dolai, Staten Island, NY (US); Christopher Corbo, Staten Island, NY (US); Saadyah Averick, Staten Island, NY (US); Amit Mogha, Staten Island, NY (US); Shawon Debnath, Staten Island, NY (US)

(73) Assignee: RESEARCH FOUNDATION OF THE CITY UNIVERSITY OF NEW YORK, New York, NY (US)

( * ) Notice: Subject to any disclaimer, the term of this patent is extended or adjusted under 35 U.S.C. 154(b) by 0 days.

(21) Appl. No.: 13/581,020

(22) PCT Filed: Feb. 25, 2011

(86) PCT No.: PCT/US2011/026308
§ 371 (c)(1),
(2), (4) Date: Apr. 10, 2013

(87) PCT Pub. No.: WO2011/106691
PCT Pub. Date: Sep. 1, 2011

(65) Prior Publication Data
US 2013/0190256 A1  Jul. 25, 2013

Related U.S. Application Data

(60) Provisional application No. 61/308,362, filed on Feb. 26, 2010.

(51) Int. Cl.
| | |
|---|---|
| *A61K 31/4192* | (2006.01) |
| *A61K 31/7056* | (2006.01) |
| *C07H 15/26* | (2006.01) |
| *C07D 249/04* | (2006.01) |
| *C07H 13/04* | (2006.01) |
| *C07C 49/255* | (2006.01) |
| *C07C 69/42* | (2006.01) |
| *C07C 69/716* | (2006.01) |
| *C07C 233/18* | (2006.01) |
| *C07H 15/08* | (2006.01) |
| *C07H 7/06* | (2006.01) |

(52) U.S. Cl.
CPC ......... *C07H 13/04* (2013.01); *A61K 31/4192* (2013.01); *A61K 31/7056* (2013.01); *C07C 49/255* (2013.01); *C07C 69/42* (2013.01); *C07C 69/716* (2013.01); *C07C 233/18* (2013.01); *C07D 249/04* (2013.01); *C07H 7/06* (2013.01); *C07H 15/08* (2013.01); *C07H 15/26* (2013.01)

(58) Field of Classification Search
CPC ................................. C07H 13/04; C07H 7/06
USPC ........................................................ 536/4.1
See application file for complete search history.

(56) References Cited

U.S. PATENT DOCUMENTS

| | | | |
|---|---|---|---|
| 5,936,075 A | 8/1999 | Nilsson | |
| 8,487,139 B2 * | 7/2013 | Raja | A61K 8/37 548/255 |
| 9,012,411 B2 * | 4/2015 | Jacob | A61K 31/12 514/159 |
| 2003/0153512 A1 | 8/2003 | Hergenhahn et al. | |
| 2007/0060644 A1 * | 3/2007 | Vander Jagt | A61K 31/12 514/475 |

FOREIGN PATENT DOCUMENTS

| | | | | |
|---|---|---|---|---|
| CN | 101524546 A | * | 9/2009 | A61K 47/48 |
| WO | WO2004/031122 | * | 4/2004 | C07C 69/52 |

OTHER PUBLICATIONS

Dubey et al., "Design, synthesis and characterization of some bioactive conjugates of curcumin with glycine, glutamic acid, valine and demethylenated piperic acid and study of their antimicrobial and antiproliferative properties" European Journal of Medicinal Chemistry (2008) vol. 43 pp. 1837-1846.*
Shi et al., "Synthesis of Monofunctional Curcumin Derivatives, Clicked Curcumin Dimer, and a PAMAM Dendrimer Curcumin Conjugate for Therapeutic Applications" Organic Letters (2007) vol. 9 No. 26 pp. 5461-5464.*
English abstract and machine translation of WO2004/031122 above (2004) downloaded from Chemical Abstracts database HCAPLUS, and espace.net.*
English abstract of CN101524546A above, downloaded from Chemical Abstracts database HCAPLUS.*
DuBois et al., "Novel, Stereoselective Synthesis of 2-Amino Saccharides," J. Am. Chem. Soc., vol. 119, 3179-3180 (1997).

* cited by examiner

*Primary Examiner* — Eric Olson
(74) *Attorney, Agent, or Firm* — Hoffmann & Baron, LLP

(57) ABSTRACT

The invention relates to novel curcumin derivatives in which one or two of the phenolic groups have been modified.

9 Claims, 3 Drawing Sheets

CURCUMIN DERIVATIVES

CROSS-REFERENCE TO RELATED APPLICATION

This application is the U.S. National Phase of, and claims priority to, International Patent Application Number PCT/US2011/026308 filed 25 Feb. 2011, which claims the benefit of U.S. Provisional Application No. 61/308,362, filed Feb. 26, 2010, each of which is incorporated by reference.

BACKGROUND OF THE INVENTION

There is a vital need to find drugs that halt or reverse Alzheimer's disease (AD). AD presently affects 18 million people worldwide. The human and financial costs of AD in the US is expected to exceed $150 billion in 2005. FDA approved medications treat symptoms, but do not alter AD progression.

The hallmarks of AD are inter-neuronal plaques consisting of precipitates or aggregates of amyloid beta protein (Aβ), and intra-neuronal neurofibrillary tangles (NFTs) of tau protein. The major target for drug discovery for AD has been Aβ that forms insoluble senile plaques. Although the etiology of AD is not fully understood, the Aβ amyloid cascade hypothesis is the most common view of the pathological pathway of AD in which the generation of Aβ and accumulation of Aβ aggregates in the brain initiate the disease process. It is supported by genetic evidence that mutations leading to increased production of Aβ leads to familial AD. Agents that dissolve Amyloid plaque or reduce plaque burden via other mechanisms are considered potential Alzheimer's drugs.

Development of Water-Soluble Curcumin Derivatives for AD

*Curcuma longa* commonly referred to as "turmeric" is used as a spice in South Asian cooking, as a cosmetic and in the ancient Ayurvedic system of medicine[2-4]. There has recently been tremendous interest in curcumin, [(1E,6E)-1,7-bis(4-hydroxy-3-methoxyphenyl)hepta-1,6-diene 3,5-dione] the primary active ingredient in turmeric, because it has been shown to have antioxidant[5], anticancer[6], anti-inflammatory[7], and potent anti-AD activity[8]. Encouraging results have been published regarding neuroprotective effects of curcumin and ongoing pilot clinical trials have been initiated[9]. Curcumin has been shown to reduce pathology in AD mouse models overproducing Aβ[10-14] and bisdemethoxycurcumin was reported to improve the innate immune system by enhancing phagocytosis of Aβ[15]. Curcumin appears to have multiple neuroprotective mechanisms including inhibition of inflammation, suppression of Aβ production, reduction of reactive oxygen species by chelating metals, inhibition of stress pathways and induction of heat shock proteins[8, 16-18]. One of the major limitations of using curcumin as a drug is its poor water and plasma solubility; even doses as high as 8 g of curcumin per day administered to human subjects result in an average peak serum concentration of ~1.77 μM of curcumin[19,20].

SUMMARY OF THE INVENTION

In one embodiment, the invention relates to a curcumin derivative having the formula I:

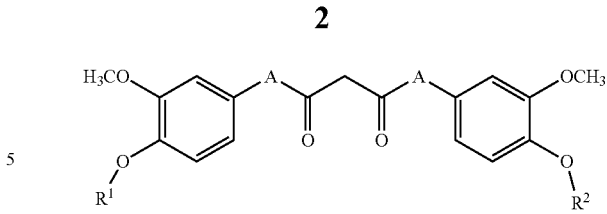

wherein:

A is —CH$_2$—CH$_2$— or —CH=CH—;

R$^1$ represents H or L$^1_{m1}$-Y$^1$;

R$^2$ represents H or L$^2_{m2}$-Y$^2$;

L$^1$ and L$^2$ are independently

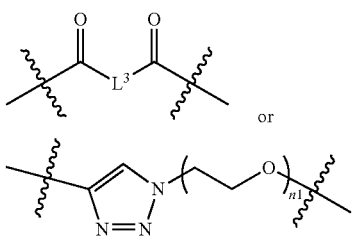

m1 and m2 are independently 0 or 1;

n1 is independently 0 or an integer from 1 to 50;

L$^3$ is independently a saturated or unsaturated, branched or unbranched hydrocarbyl with 1 to 12 carbon atoms;

Y$^1$ and Y$^2$ independently represent —OH; a saccharide with 1 to 51 monosaccharide units; —NH—(CH$_2$CH$_2$—O)$_{n2}$—R$^3$; —O—(CH$_2$CH$_2$—O)$_{n2}$—R$^3$; —CH=CH$_2$; or —C≡CH;

R$^3$ independently represents a saturated, unbranched hydrocarbyl with 1 to 4 carbon atoms; and n2 independently represents an integer from 5 to 50;

with the proviso that if R$^1$=R$^2$, then R$^1$=R$^2$≠H;

with the proviso that if Y$^1$ is OH, then L$^1$ is

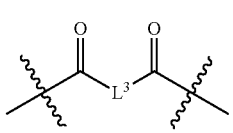

and R$^2$ is not H;

with the proviso that if Y$^2$ is OH, then L$^2$ is

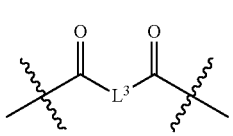

and R$^1$ is not H;

with the proviso that if m1 is 0, then Y$^1$ is not a saccharide;

with the proviso that if m2 is 0, then Y$^2$ is not a saccharide;

with the proviso that if Y$^1$ is —NH—(CH$_2$CH$_2$—O)$_{n2}$—R$^3$ or —O—(CH$_2$CH$_2$—O)$_{n2}$—R$^3$, then L$^1$ is

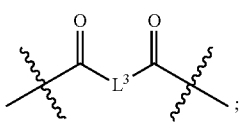

and with the proviso that if $Y^2$ is —NH—$(CH_2CH_2—O)_{n2}$—$R^3$ or —O—$(CH_2CH_2—O)_{n2}$—$R^3$, then $L^2$ is

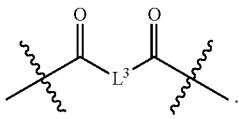

In another embodiment, the invention relates to a method of treating Ahzheimer's disease in a patient by administering a curcumin derivative having formula I.

DETAILED DESCRIPTION

Figure 1:
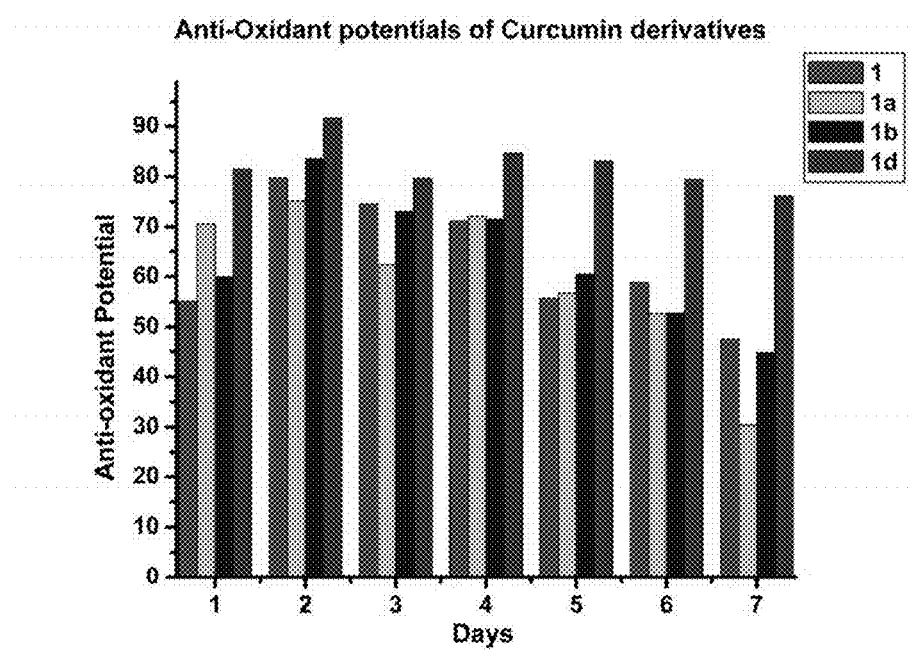
FIG. 1 depicts anti-oxidant potentials of Curcumin 1, Curcumin mono-alkyne 1a, Curcumin mono-carboxylic acid 1b and sweet curry 1d in water. Compound 1d is a much better antioxidant than Curcumin 1 as well as other curcumin derivatives (1a,1b) in an aqueous medium which serves as a model for physiological conditions (plasma). Sweet curry 1d is also superiorly soluble in water compared to Curcumin and derivatives 1a and 1b.
Figure 2:
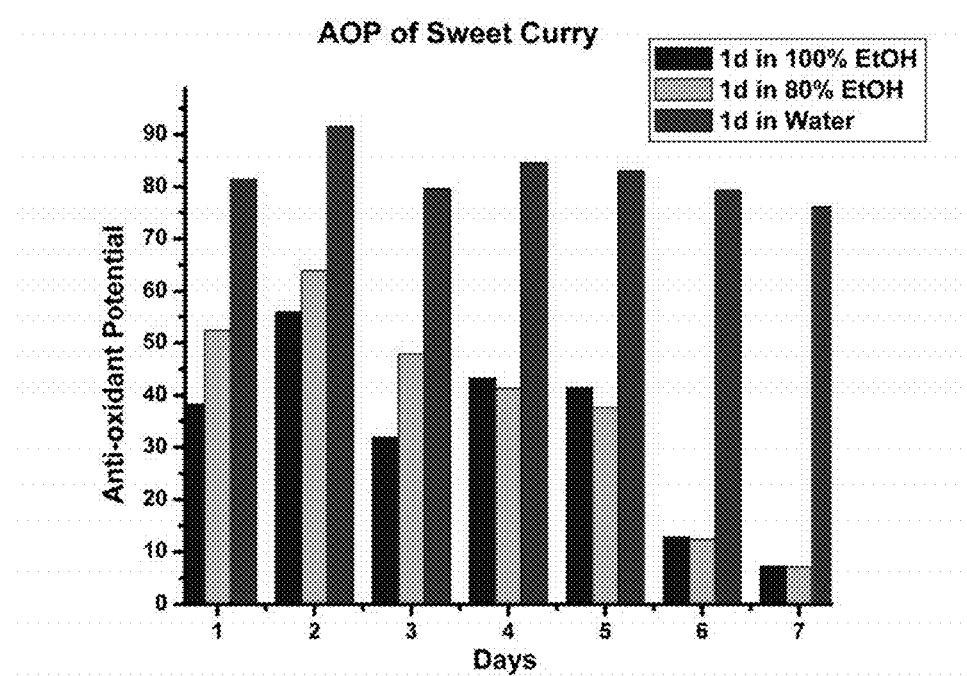
FIG. 2 depicts AOP of sweet curry in water and ethanol.
Figure 3:
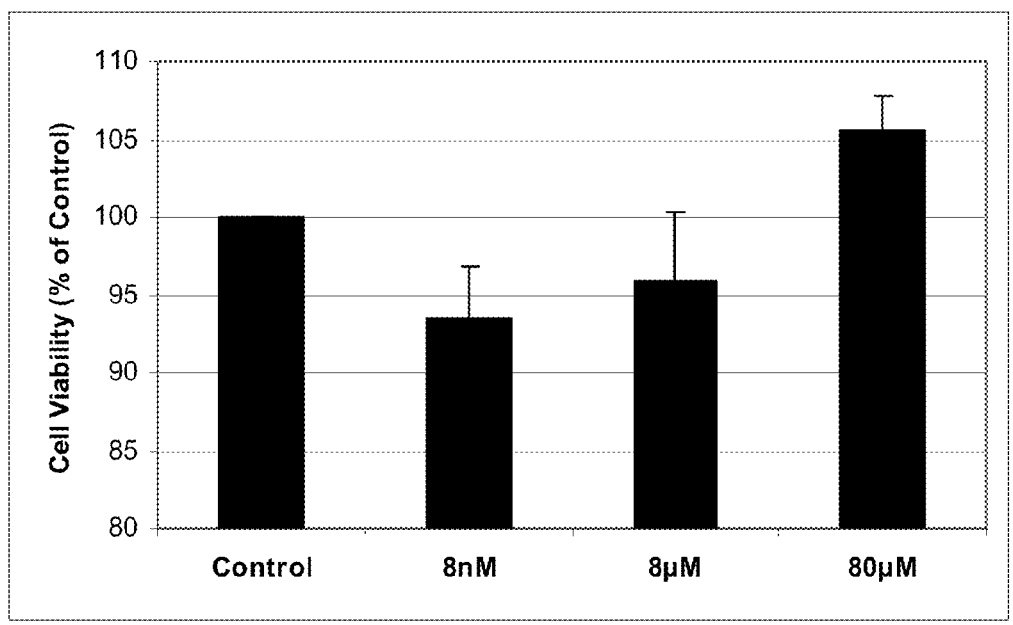
FIG. 3 depicts a Cell Viability Chart of sweet curry at different concentrations.

The invention relates to novel curcumin derivatives in which one or two of the phenolic groups have been modified.

The curcumin derivative is represented by formula I below:

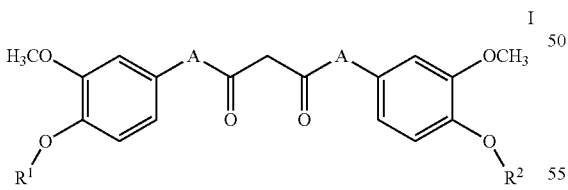

In formula I, A represents —$CH_2$—$CH_2$— or —CH=CH—. When A is —$CH_2$—$CH_2$—, the compound is a tetrahydrocurcumin derivative. When A is —CH=CH—, the compound is a curcumin derivative.

$R^1$ represents H (hydrogen) or $L^1_{m1}$-$Y^1$. $R^2$ represents H (hydrogen) or $L^2_{m2}$-$Y^2$. When only one of $R^1$ and $R^2$ represents H, then only one of the phenolic groups on the curcumin derivative is modified. When both $R^1$ and $R^2$ are not H, then both of the phenolic groups on the curcumin derivative are modified.

$L^1$ and $L^2$ are linkers that independently represent

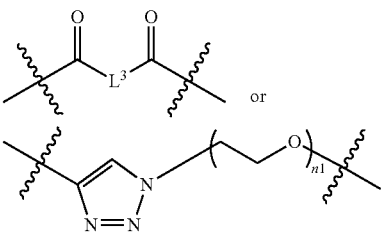

In one embodiment, $L^1$ and $L^2$ both represent:

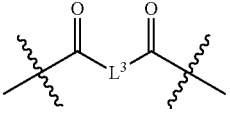

In another embodiment, $L^1$ and $L^2$ both represent:

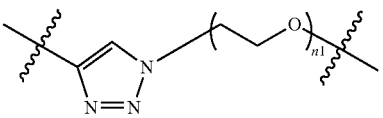

In a third embodiment, $L^1$ represents

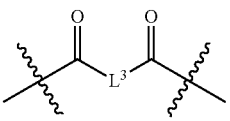

and $L^2$ represents

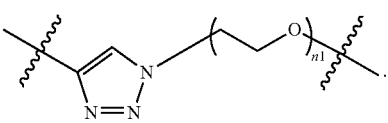

Conversely, in another embodiment, $L^2$ represents

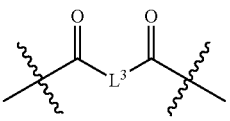

and $L^1$ represents

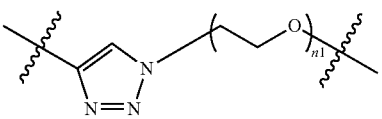

The letters m1 and m2 are independently 0 or 1. Therefore, when m1 is 0, then there is no linker $L^1$, so $R^1=Y^1$. Likewise, when m2 is 0, then there is no linker $L^2$, so $R^2=Y^2$.

When m1 is 1 and $L^1$ is

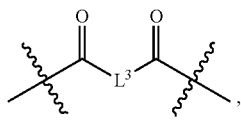

then $L^3$ is independently a saturated or unsaturated, branched or unbranched hydrocarbyl with 1 to 12 carbon atoms. The carbon atoms of the hydrocarbyl can all be saturated, or can all be unsaturated. Alternatively, the chain can comprise a mixture of saturated and unsaturated carbon atoms. The unsaturated hydrocarbyl chains contain one or more double and/or triple bonds.

Some examples of suitable, saturated straight-chained hydrocarbyl chains include methyl, ethyl, n-propyl, n-butyl, n-pentyl, n-hexyl, and dodecyl chains. Preferred straight chain alkyl groups include methyl and ethyl. Some examples of suitable, unsaturated straight-chained hydrocarbyl chains include 3-butenyl, 1,3-heptadienyl, and 2-dodecynyl chains.

Some examples of suitable saturated, branched alkyl groups include iso-propyl, iso-butyl, sec-butyl, t-butyl, 1-methylbutyl, 2-methylbutyl, 3-methylbutyl(isopentyl), 1,1-dimethylpropyl, 1,2-dimethylpropyl, 2,2-dimethylpropyl(neopentyl), 1-methylpentyl, 2-methylpentyl, 3-methylpentyl, and 4-methylpentyl. Preferred branched alkyl groups include isopropyl and t-butyl. Some suitable examples of unsaturated, branched alkyl groups include 1-methyl-4-pentenyl and 2-ethyl-1,8-decadienyl.

When, m2 is 1 and $L^2$ is

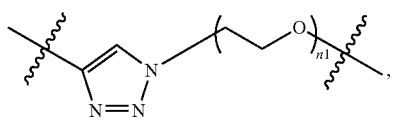

then n1 is independently 0 or an integer from 1 to 50. All integers from 1 to 50 are contemplated, e.g., 1, 2, 3, 4, . . . , 46, 47, 48, 49, and 50. The preferred minimum value of n1 is 2, more preferably 3. The preferred maximum value of n1 is 20, more preferably 12.

$Y^1$ and $Y^2$ independently represent —OH; a saccharide with 1 to 51 monosaccharide units; —NH—$(CH_2CH_2—O)_{n2}$—$R^3$; —O—$(CH_2CH_2—O)_{n2}$—$R^3$; —CH=CH$_2$ or —C≡CH. The preferred number of monosaccharide units are 1, 2, and 3. The most preferred saccharide is a monosaccharide.

Saccharides are well known in the art and include monosaccharides, disaccharides, trisaccharides, oligosaccharides, and polysaccharides with a maximum of 51 monosaccharide units. Therefore, saccharides such as dextran which contain over 51 monosaccharide units are excluded from the present invention.

Monosaccharide units include, but are not limited to, glucose (dextrose), fructose (levulose), galactose, allose, altrose, mannose, gulose, idose, talose, xylose, and ribose. The preferred monosaccharides units and monosaccharides are glucose and galactose.

Disaccharide units include, but are not limited to, sucrose, lactose, lactulose, maltose, trehalose, and cellobiose.

Saccharides of the invention must be connected to the phenolic group of the curcumin derivative through a linker. Therefore, if m1 is 0, then $Y^1$ is not a saccharide. Likewise, if m2 is 0, then $Y^2$ is not a saccharide.

The linker $L^1$ or $L^2$ can be attached to any —OH group on an end monosaccharide unit of the saccharide.

When $Y^1$ or $Y^2$ is a monosaccharide, the monosaccharide may or may not be a deoxy-aminosaccharide. When $Y^1$ or $Y^2$ is a deoxy-aminosaccharide, the monosaccharide may or may not be bonded to $L^1$ or $L^2$ through the amino group of the deoxy-aminosaccharide.

When $Y^1$ or $Y^2$ is a di-, tri-, or oligosaccharide (4-51), any one or more of the monosaccharide units may be a deoxyaminosaccharide unit. If the proximal monosaccharide unit in a di-, tri-, or oligosaccharide is a deoxy-aminosaccharide and m1 or m2 is 1, the di-, tri-, or oligosaccharide may or may not be bonded to $L^1$ or $L^2$ through the amino group of the deoxy-aminosaccharide unit.

Monosaccharides that are deoxy-aminosaccharides are known in nature, and may also be synthesized by methods known in the art, such as those described in Du Bois at al., J. Am. Chem. Soc. 119, 3179-3180 (1977), and references cited therein. Di-, tri-, and oligosaccharides in which the proximal monosaccharide unit is a deoxy-aminosaccharide are also known in nature, and may also be synthesized by methods known in the art, such as those described by Nilsson, U.S. Pat. No. 5,936,075.

$R^3$ independently represents a saturated, unbranched hydrocarbyl with 1 to 4 carbon atoms. Examples of saturated, unbranched hydrocarbyls are methyl, ethyl, propyl, and butyl.

The letter n2 independently represents an integer from 5 to 50. All integers from 5 to 50 are contemplated, e.g., 5, 6, 7, 8, . . . , 47, 48, 49, 50. The preferred minimum value of n2 is 6, more preferably 5. The preferred maximum value of n2 is 20, more preferably 12.

The main independent claim contains certain provisos. For example, if $R^1=R^2$, then $R^1$ and $R^2$ are not H. This excludes the possibility of the compound being unsubstituted curcumin or tetrahydrocurcumin.

In another proviso, if $Y^1$ is OH, then $L^1$ is

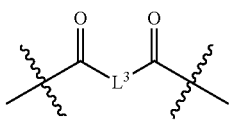

and $R^2$ is not H. Likewise, if $Y^2$ is OH, then $L^2$ is

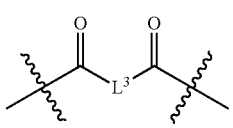

and $R^1$ is not H.

If $Y^1$ is —NH—$(CH_2CH_2—O)_{n2}$—$R^3$ or —O—$(CH_2CH_2—O)_{n2}$—$R^3$, then $L^1$ is

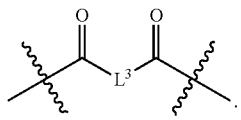

Likewise, if $Y^2$ is —NH—$(CH_2CH_2—O)_{n2}$—$R^3$ or —O—$(CH_2CH_2—O)_{n2}$—$R^3$, then $L^2$ is

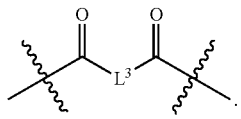

A list of preferred compounds of the invention is provided in Table I.

In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any two, three, or four of the members, e.g., a and c; a, d, and e; b, c, d, and e; etc.

In some cases, the members of a First group of parameters, e.g., a, b, c, d, and e, may be combined with the members of a second group of parameters, e.g., A, B, C, D, and E. Any member of the first group or of a sub-group thereof may be combined with any member of the second group or of a sub-group thereof to form additional groups, i.e., b with C; a and c with B, D, and E, etc.

For example, in the present invention, groups of various parameters are defined (e.g. A, $R^1$, $R^2$, $Y^1$, $Y^2$, m1, m2, $L^1$, and $L^2$). Each group contains multiple members. For example, $Y^1$ and $Y^2$ independently represent —OH; a saccharide with 1 to 51 monosaccharide units; —NH—$(CH_2CH_2—O)_{n2}$—$R^3$; —O—$(CH_2CH_2—O)_{n2}$—$R^3$; —CH=$CH_2$; or —C≡CH. Each member may be combined with each other member to form additional sub-groups, e.g., —OH and a monosaccharide; —OH and —CH=$CH_2$; or a monosaccharide, —NH—$(CH_2CH_2—O)_{n2}$—$R^3$, and —C≡CH.

The instant invention further contemplates embodiments in which each element listed under one group may be combined with each and every element listed under any other group unless specifically excluded by a proviso. For example, $Y^1$ and $Y^2$ are identified above as independently representing —OH; a saccharide with 1 to 51 monosaccharide units; —NH—$(CH_2CH_2—O)_{n2}$—$R^3$; —O—$(CH_2CH_2—O)_{n2}$—$R^3$; —CH=$CH_2$, or —C≡CH. $L^1$ and $L^2$ are identified above as linkers independently representing

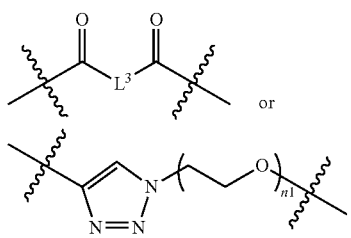

Each element of $Y^1$ and $Y^2$ (—OH; a saccharide with 1 to 51 monosaccharide units; —NH—$(CH_2CH_2—O)_{n2}$—$R^3$; —O—$(CH_2CH_2—O)_{n2}$—$R^3$; —CH=$CH_2$; or —C≡CH) can be combined with each and every element of $L^1$ and $L^2$

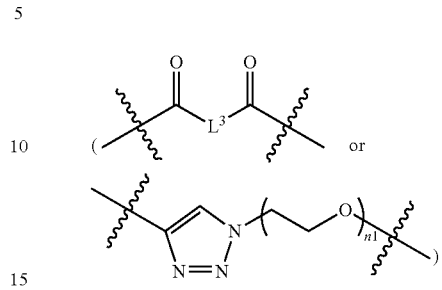

unless specifically excluded with proviso language.

For example, in one embodiment, $Y^1$ may be —OH; $L^1$ may be

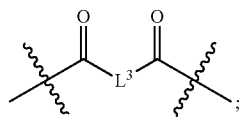

$Y^2$ may be —O—$(CH_2CH_2—O)_{n2}$—$R^3$; and $L^2$ may be

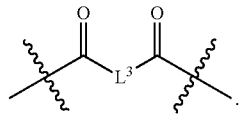

Alternatively, $Y^1$ may be a trisaccharide; $L^1$ may be

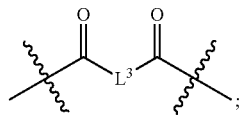

$Y^2$ may be —OH; and $L^2$ may be

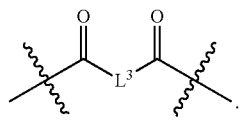

Similarly, a third group is A, in which the elements are defined as —$CH_2$—$CH_2$— or —CH=CH—. Each of the above embodiments may be combined with each and every element of A. For example, in the embodiment wherein $Y^1$ may be —OH; $L^1$ may be

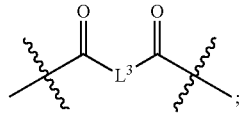

$Y^2$ may be $-O-(CH_2CH_2-O)_{n2}-R^3$; and $L^2$ may be

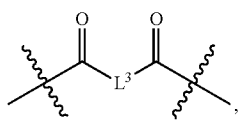

A may be —$CH_2$—$CH_2$— (or any other chemical moiety within the element of A).

With each group, it is specifically contemplated that any one or more members can be excluded. For example, if $Y^1$ is defined as —OH; a saccharide with 1 to 51 monosaccharide units; —NH—$(CH_2CH_2-O)_{n2}$—$R^3$; —O—$(CH_2CH_2-O)_{n2}$—$R^3$; —CH=$CH_2$, or —C≡CH; it is also contemplated that $Y^1$ is defined as a saccharide with 1 to 51 monosaccharide units; —O—$(CH_2CH_2-O)_{n2}$—$R^3$; or —C≡CH.

The compounds of this invention are limited to those that are chemically feasible and stable. Therefore, a combination of substituents or variables in the compounds described above is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

All stereoisomers of the compounds of the instant invention are contemplated, either in admixture or in pure or substantially pure form. The definition of compounds according to the invention embraces all the possible stereoisomers and their mixtures; it also embraces the racemic forms and the isolated optical isomers having the specified activity. The racemic forms can be resolved by physical methods, such as, for example, fractional crystallization, separation, or crystallization of diastereomeric derivatives or separation by chiral column chromatography. The individual optical isomers can be obtained from the racemates from the conventional methods, such as, for example, salt formation with an optically active acid followed by crystallization.

A list following the word "comprising" is inclusive or open-ended, i.e., the list may or may not include additional unrecited elements. A list following the words "consisting of" is exclusive or closed ended, i.e., the list excludes any element not specified in the list.

All numbers in the specification are approximate unless indicated otherwise.

The method of treating a condition, disorder or disease with a chemical compound or a chemical composition includes the use of the chemical compound or chemical composition in the manufacture of a medicament for the treatment of the condition, disorder or disease. A compound or a group of compounds said to be effective in treating a condition, disorder or disease includes the compound or group of compounds for use in treating the condition, disorder or disease.

Synthesis of Compounds

The water/plasma solubility of curcumin is improved by selective covalent modification of one or both of its phenolic —OH groups by attaching water-soluble molecules such as polyethylene glycol (PEG) and sugar derivatives to produce covalent conjugates. The sugar/PEG component of the conjugate confers improved water/plasma solubility to the curcumin component. Several series of conjugates with varying hydrophilic-lipophilic balance (HLB) are synthesized to optimize the plasma solubility and the ability to cross the blood-brain barrier (BBB). Novel mono-functional curcumin derivatives have been synthesized in which one of the phenolic groups of curcumin has been chemically modified with reactive groups (e.g., azidyl, alkynyl and carboxyl groups)[21].

Preferably, direct one/two step covalent modification of curcumin is utilized to produce the mono-functional and di-functional derivatives in good yields. The synthesis of mono-functional curcumin derivatives has two advantages; (1) the presence of at least one free phenolic group is necessary for the biological activity of many antioxidants like curcumin[5] as mono-functional derivatives of curcumin retain their ability to bind and dissociate amyloid fibrils in vitro[21, 22], and (2) high yields: conjugates produced using mono-functional derivatives result in soluble products in high yields.

Optionally, the carboxylate, azidyl, or alkynyl groups serve as covalent functional handles for attaching curcumin to biocompatible water-solubilizing molecules such as sugars and PEG. The glucuronidation of curcumin in vivo is another possible reason for the observation of very low plasma levels of the compound[23]. In the curcumin-glucuronide derivative, one of the phenolic groups of curcumin is enzymatically modified and the derivative is negatively charged. Therefore the derivative would not be likely to cross the blood brain barrier. Furthermore, the curcumin derivatives (in which one or both of the phenolic —OH groups of curcumin is covalently modified) will resist glucurodination because one or both of the phenolic —OH groups is blocked, it is also highly likely that they will not fit the active site of the glucuridination enzyme.

Three chemistries are employed: (a) Azide derivatives of carbohydrates/oligo-ethylene glycol (OEG) will be coupled with curcumin alkyne under the Sharpless "click" conditions to produce triazole derivatives of Curcumin, (b) OEG amines/carbohydrate amines will be condensed with a carboxylic acid derivatives of curcumin under amide coupling conditions to produce amide conjugates of Curcumin, (c) OEG/carbohydrates can also be coupled to Curcumin carboxylic acid via esterification. Well-defined efficient reactions such as amide couplings, esterifications or [3+2] azide-alkyne cycloaddition in preparing curcumin conjugates are used.

In the "clicked" derivatives of curcumin, curcumin is connected via an ether bond and a triazole linker to the sugar/OEG component. The ether and triazole links present in these conjugates are extremely stable to hydrolysis, it is anticipated that these derivatives can be administered orally and would survive acid in the gastrointestinal tract. It is also possible to administer these derivatives intravenously (injectible formulation). A "clicked" sugar curcumin conjugate with vastly improved water solubility has been synthesized. The amide and ester conjugates of curcumin and OEGs/sugars have ester links in their structures connecting the water solublizing component to curcumin. These links are labile and would undergo hydrolysis over time to produce curcumin, thus allowing us to explore a "prodrug" approach. The amide and ester conjugates may undergo acid hydrolysis in the gastrointestinal tract, and therefore may be administered either as an inhalable formulation or as an injectable. The triazole (sugar and OEG) conjugates (with improved water/plasma solubility) which are resistant to acid hydrolysis can be administered orally. The "clicked" sugar conjugate of curcumin has a direct water solubility of ~0.2 mmol, in a tau oligomer dissolution assay the mono-functional curcumin derivatives work at a micromolar concentrations, a therapeutically effective concentration can therefore be achieved in a facile fashion using this technology. It may also be possible to synthesize and screen a range of carbohydrate derivatives of curcumin to optimize brain uptake of the carbohydrate conjugates via the glucose transport mechanism[24].

Scheme 1: Schematic synthesis of Curcumin-sugar conjugate via "click" reaction.
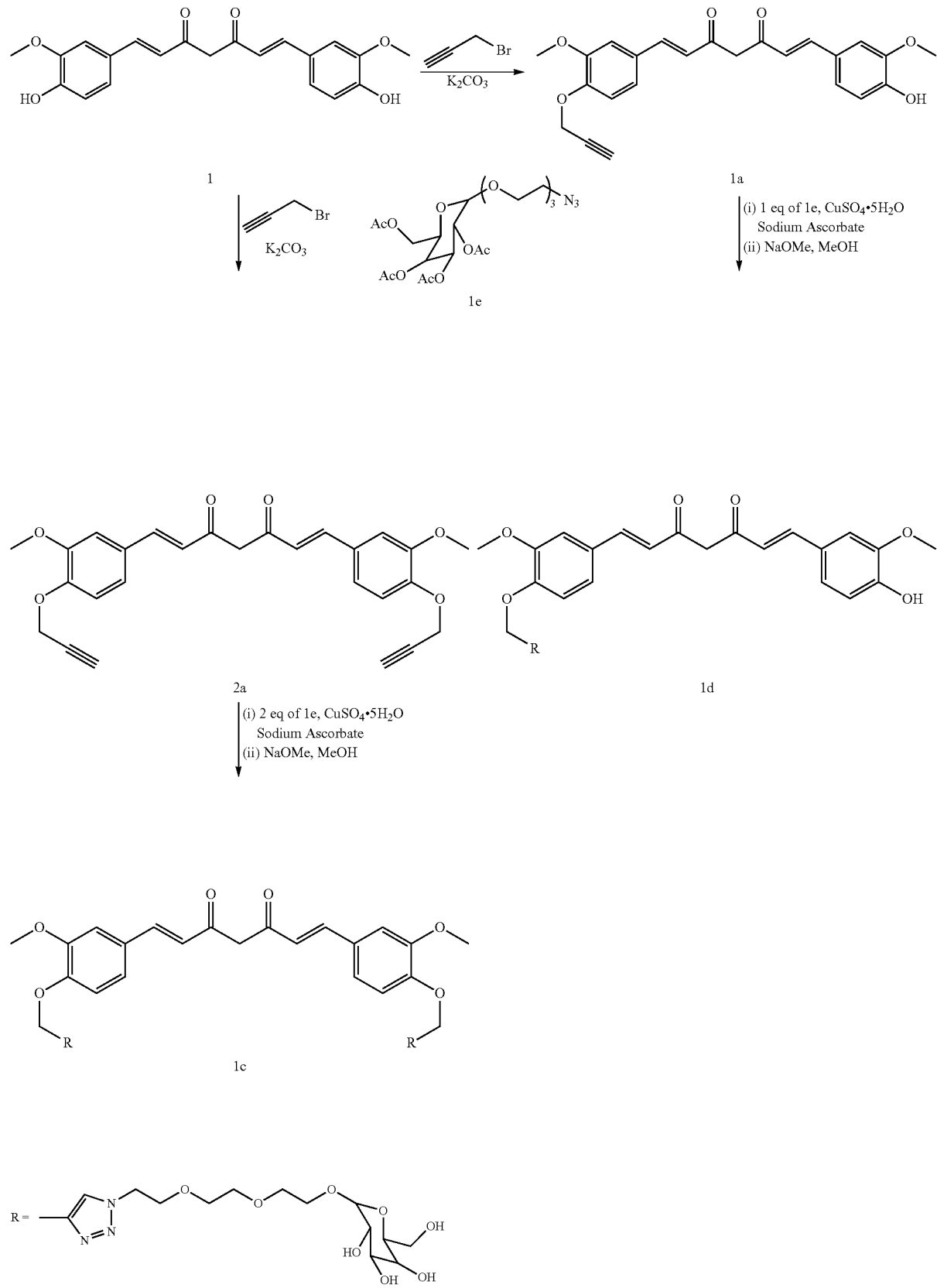

Scheme 2: Synthetic scheme of Curcumin-sugar conjugate (via esterification).
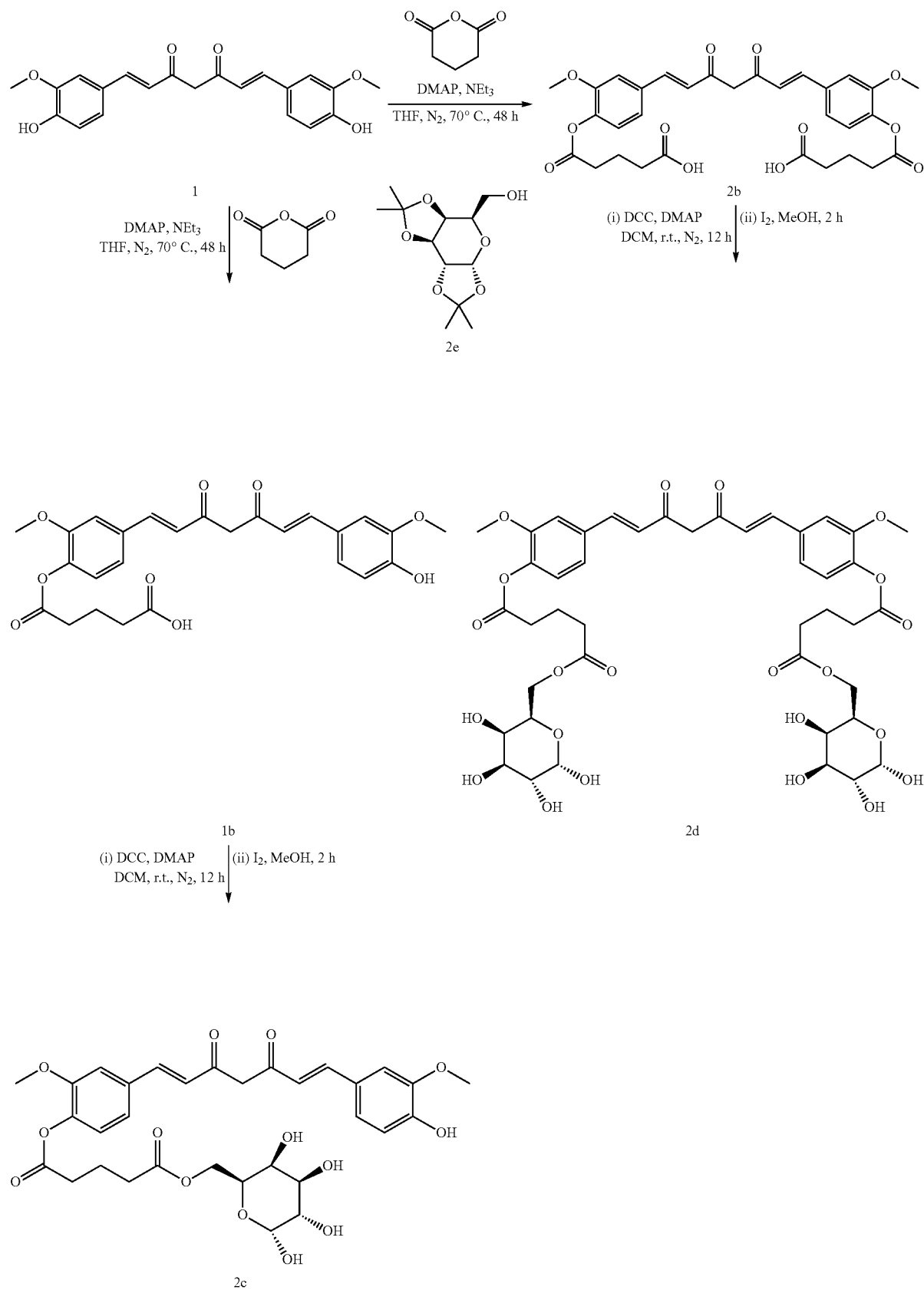

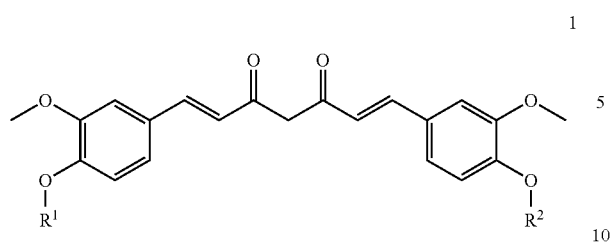
Curcumin
R¹ = R² = H
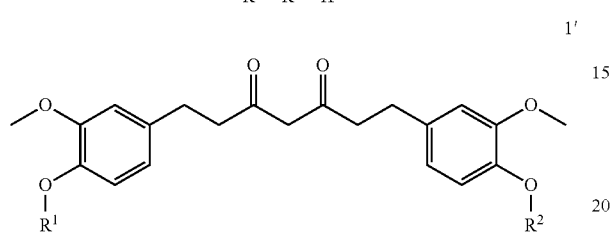
Tetrahydro Curcumin
R¹ = R² = H
TABLE 1
List of possible R groups attached via phenolic —OH groups
| Entry Number | Structures of the considerable groups |
|---|---|
| 1 | R¹ = H  R² = —≡ |
| 2 | R¹ = R² = —≡ |
| 3 | 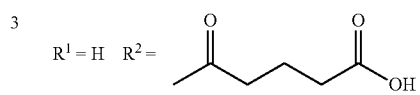 |
| 4 | 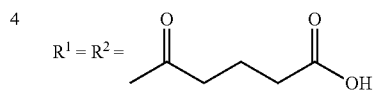 |
| 5 | 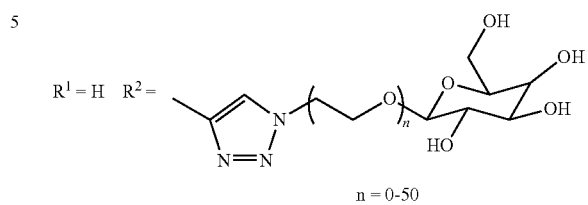  n = 0-50 |
| 6 | 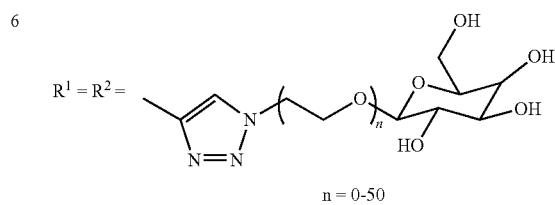  n = 0-50 |

TABLE 1-continued
List of possible R groups attached via phenolic —OH groups
Entry Number  Structures of the considerable groups
7 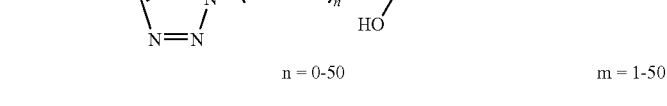
n = 0-50    m = 1-50
8 
n = 0-50    m = 1-50
9 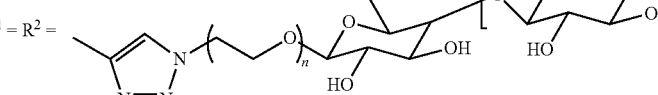
10 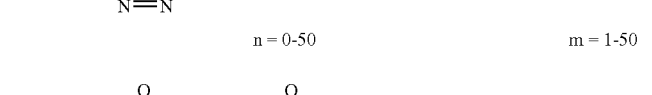
11 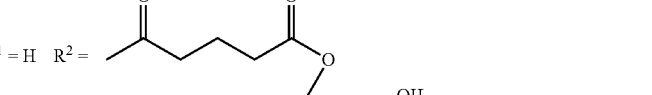
12 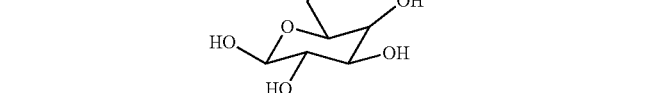
13 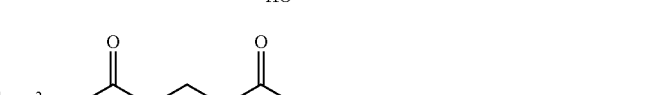
m = 1-50

TABLE 1-continued
List of possible R groups attached via phenolic —OH groups
Entry Number  Structures of the considerable groups
14  $R^1 = R^2 =$
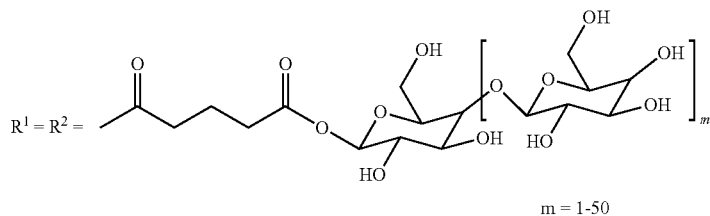
m = 1-50
15  $R^1 = H$  $R^2 =$
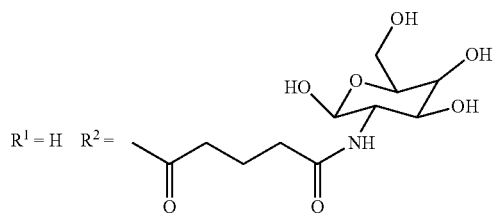 [SMILES: CC(=O)CCCC(=O)NC1C(O)OC(CO)C(O)C1O]
16  $R^1 = R^2 =$
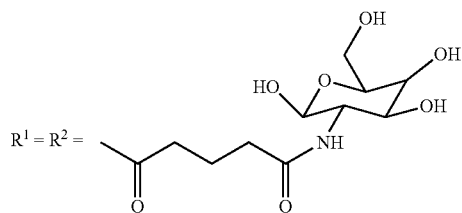 [SMILES: CC(=O)CCCC(=O)NC1C(O)OC(CO)C(O)C1O]
17  $R^1 = H$  $R^2 =$
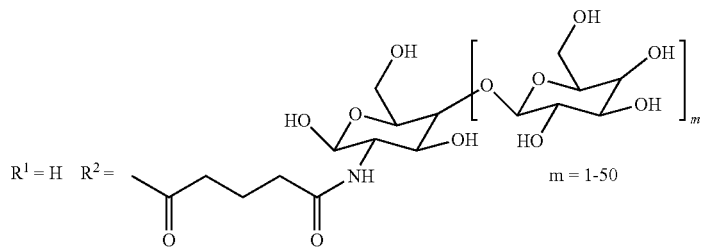
m = 1-50
18  $R^1 = R^2 =$
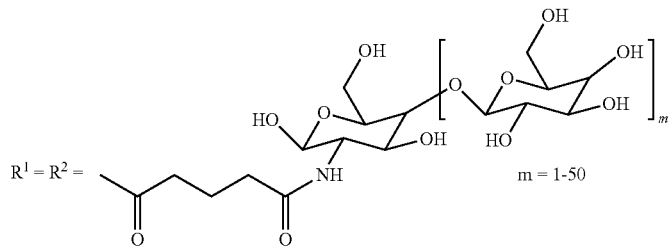
m = 1-50
19  $R^1 = H$  $R^2 =$
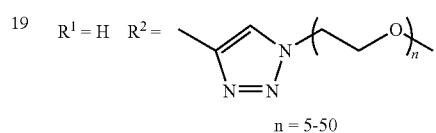
n = 5-50
20  $R^1 = R^2 =$
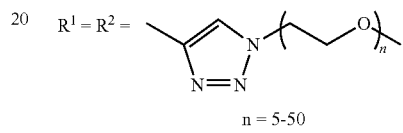
n = 5-50

TABLE 1-continued

List of possible R groups attached via phenolic —OH groups

| Entry Number | Structures of the considerable groups |
|---|---|
| 21 | $R^1 = H$  $R^2 =$ [structure with amide-PEG, n = 5-50] |
| 22 | $R^1 = R^2 =$ [structure with amide-PEG, n = 5-50] |
| 23 | $R^1 = H$  $R^2 =$ [structure with ester-PEG, n = 5-50] |
| 24 | $R^1 = R^2 =$ [structure with ester-PEG, n = 5-50] |

EXAMPLES

1. Synthesis of Curcumin mono-alkyne (1a)

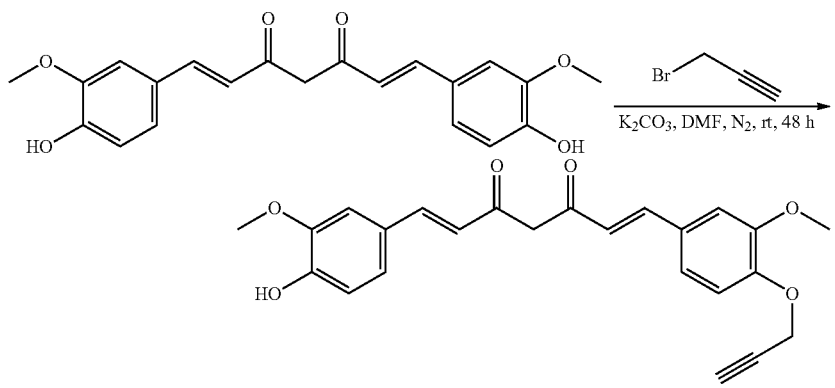

Curcumin (5 g, 13.57 mmol) and $K_2CO_3$ (1.88 g, 13.62 mmol) were added to 60 mL DMF followed by 1.62 g (13.61 mmol) of propargyl bromide. The mixture was stirred at room temperature under $N_2$ for 48 h, $H_2O$ was added to the mixture and the solvent was removed under vacuum. The product was purified by column chromatography, eluting with $CHCl_3$:hexane 90:10. Yield: 47%. $^1H$ NMR (600 MHz, $CDCl_3$), δ (ppm): 2.54 (s, 1H); 3.94 (d, 6H); 4.81 (d, 2H); 5.82 (d, 1H); 5.93 (d, 1H); 6.47-6.52 (t, 2H); 6.93-7.15 (m, 6H); 7.59-7.61 (d, 2H). $^{13}C$ NMR (150 MHz, $CDCl_3$), δ (ppm): 30.73; 30.77; 31.38; 31.40; 36.50; 55.70; 55.72; 55.76, 56.35; 101.44; 109.97; 110.01; 110.30; 113.39; 113.40; 115.14; 115.17; 121.22; 121.27; 121.94; 122.00; 122.25; 122.30; 122.85; 122.86; 127.13; 127.18; 128.93; 139.90; 139.92; 140.83; 140.86; 147.23; 148.33; 148.40; 148.46; 149.44; 162.74; 162.80; 182.57; 183.73. MS (ESI) calcd. for $C_{24}H_{22}O_6$: 406.43; found: 407.2 $[M+H]^+$, 445.2 $[M+K]^+$.

2. Synthesis of Protected Curcumin-"Clicked"-mono-galactose

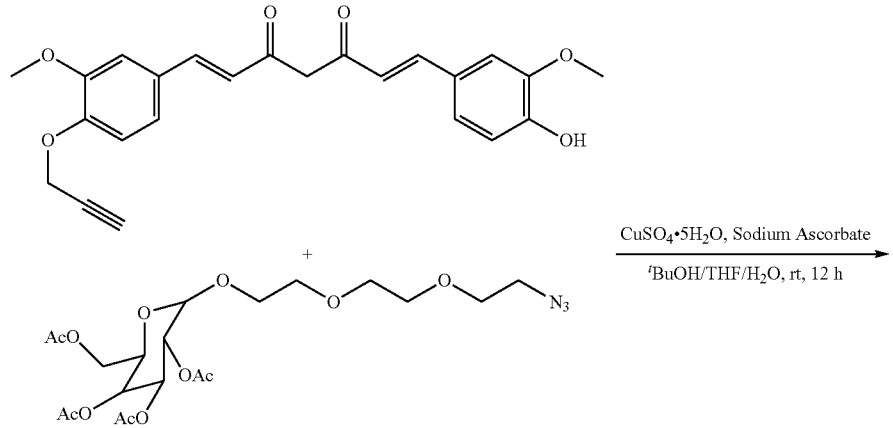

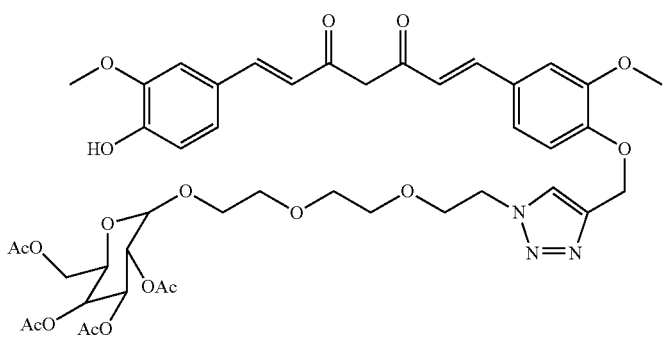

Curcumin mono-alkyne (1a) (500 mg, 1.23 mmol) was dissolved in 2 mL of THF and added to 2 mL of t-BuOH containing commercially available acetal protected Azido-Galactose derivative [2-[2-(2-Azidoethoxy)ethoxy]ethyl-2,3,4,6-Tetra-O-acetyl-D-galactopyranoside] (625 mg, 1.23 mmol) in a round bottom flask (r.b.). Fresh solutions of $CuSO_4 \cdot 5H_2O$ (76 mg, 0.3 mmol) and Sodium Ascorbate (90 mg, 0.45 mmol) were prepared separately in 1 mL of milipore water. Sodium Ascorbate solution was added to the r.b. followed by $CuSO_4$ solution and stirred for 12 hours. The reaction was stopped and the solvent was removed by evaporation. The crude product was extracted from water-chloroform mixture. The organic layer was dried over anhydrous $NaSO_4$ and solvent was evaporated. Finally the product was purified via column chromatography using Chloroform: Ethyl acetate (90:10) mixture to yield orange solid. Yield: 785 mg (70%). $^1$H NMR ($CDCl_3$, 600 MHz): δ (ppm) 1.93 (s, 3H),1.97-1.99 (d, 6H), 2.08 (s, 3H), 3.52-3.56 (m, 7H), 3.64-3.66 (m, 1H), 3.81-3.90 (m, 10H), 4.04-4.11 (m, 3H), 4.46-4.50 (m, 3H), 4.95-4.97 (dd, 1H), 5.13-5.16 (m, 1H), 5.25-5.28 (m, 2H), 5.32 (m, 1H),5.76 (s, 1H), 6.41-6.45 (m, 2H), 6.86-6.88 (d, 1H), 6.99-7.07 (m, 4H), 7.51-7.54 (m, 2H), 7.80 (s, 1H); $^{13}$C NMR ($CDCl_3$, 150 MHz): δ (ppm): 20.48, 20.54, 20.56, 20.65, 50.23, 55.82, 55.84, 61.09, 62.77, 66.92, 68.69, 69.04, 69.28, 70.07, 70.45, 70.47, 70.53, 70.75, 101.18, 101.23, 109.61, 110.30, 113.57, 114.84, 121.59, 122.15, 122.24, 122.84, 124.25, 139.99, 140.61, 143.39, 146.82, 147.93, 149.50, 149.51, 169.33, 170.04, 170.13, 170.28, 182.73, 183.52.; ESI-MS: for $C_{44}H_{53}N_3O_{18}$; calculated-911.33; observed-912.3 $[M+H]^+$.

3. Synthesis of curcumin-"Clicked"-mono-galactose (Sweet Curry) 1d

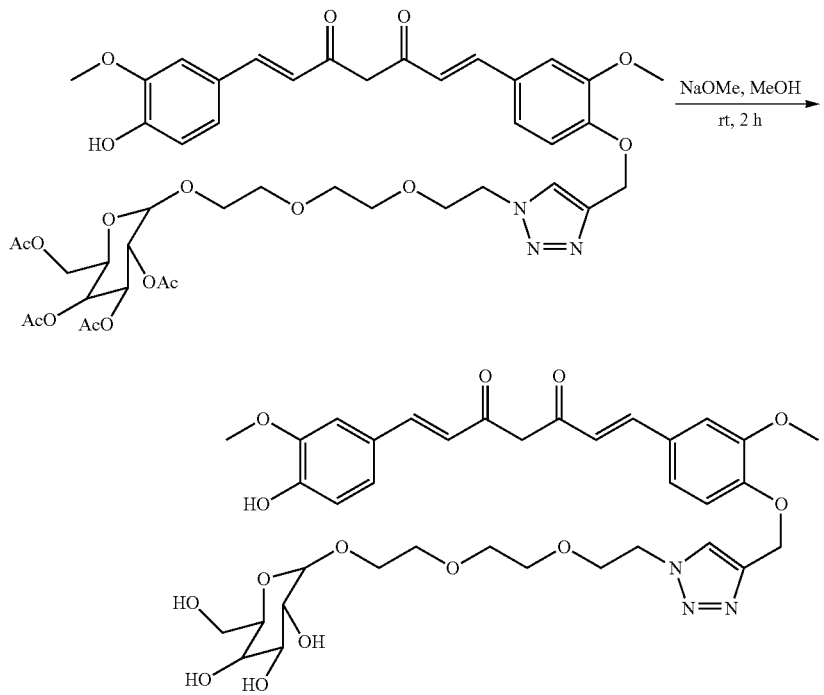

Protected curcumin-"clicked"-galactose (90 mg, 0.098 mmol) was dissolved in 3 mL of 0.3 M NaOMe in anhydrous MeOH. The mixture was stirred at room temperature for 2 hours. The pH of the solution was neutralized to pH=7 using Amberlite15 ion exchange resin and the color of the solution became light yellow from dark orange. The solution was filtered and the solvent was removed. Finally the crude product was purified via column chromatography using CHCl$_3$:MeOH (95:5) to yield 1d as a dark yellow solid. Yield: 55 mg (76%). NMR (CD$_3$OD, 600 MHz): δ (ppm) 3.01 (s, 4H), 3.09-3.13 (m, 2H), 3.17-3.19 (m, 2H), 3.25 (s, 4H), 3.27-3.29 (m, 2H), 3.32-3.42 (m, 3H), 3.47-3.52 (d, 2H), 3.54-3.57 (m, 6H), 3.62-3.64 (m, 1H), 3.86-3.87 (d, 1H), 4.25-4.27 (t, 2H), 4.91 (s, 2H), 6.28-6.35 (m, 2H), 6.48-6.49 (d, 1H), 6.76-6.91 (m, 4H), 7.22-7.25 (dd, 2H), 7.80 (s, 1H); $^{13}$C NMR (CDCl$_3$, 150 MHz): δ (ppm) 49.84, 51.48, 56.48, 56.53, 62.54, 62.79, 63.34, 69.59, 70.30, 71.09, 71.31, 71.37, 71.41, 72.50, 74.89, 76.66, 105.03, 111.79, 112.08, 115.35, 116.59, 123.55, 124.19, 126.57, 128.54, 130.50, 131.21, 141.30, 142.37, 144.47, 149.40, 150.50, 151.06, 151.37, 183.92, 185.37. ESI-MS: for C$_{36}$H$_{45}$N$_3$O$_{14}$; calculated-743.29; observed-744.3 [M+H]$^+$.

4. Synthesis of Curcumin di-alkyne

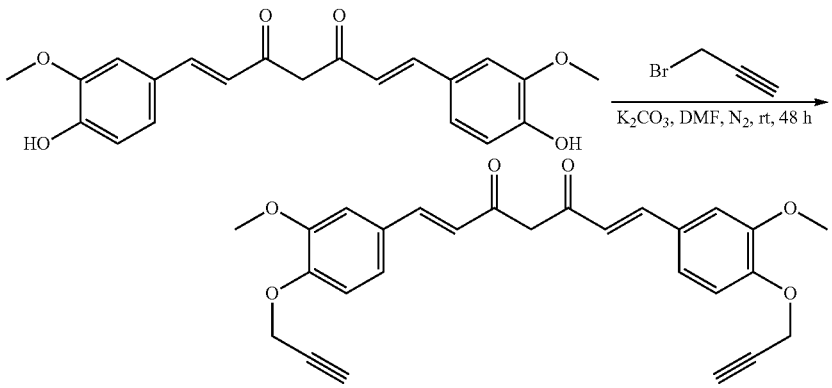

Curcumin (2 g, 5.43 mmol) and K$_2$CO$_3$ (1.52 g, 11.0 mmol) were added to 50 mL DMF followed by 1.62 g (13.61 mmol) of propargyl bromide. The mixture was stirred at room temperature under N$_2$ for 48 h, H$_2$O was added to the mixture and the solvent was removed under vacuum. The product was purified by column chromatography, eluting with CHCl$_3$:hexane 90:10. Yield: 1.78 g (74%). $^1$H NMR (600 MHz, CDCl$_3$), δ (ppm): 2.47 (s, 2H); 3.84 (s, 6H); 4.71-4.74 (m, 4H); 6.42-6.44 (d, 2H); 6.95-7.07 (m, 6H); 7.51-7.53 (d, 2H). $^{13}$C NMR (150 MHz, CDCl$_3$), δ (ppm): 55.91, 56.07, 56.58, 101.43, 110.37, 113.78, 122.05, 122.51, 129.17, 148.65, 149.60, 183.18. MS (ESI): calculated for C$_{27}$H$_{24}$O$_6$: 444.16; found: 445.1 [M+H]$^+$, 483.0 [M+K]$^+$.

5. Synthesis of Curcumin 'Clicked' di-galactose (Protected)

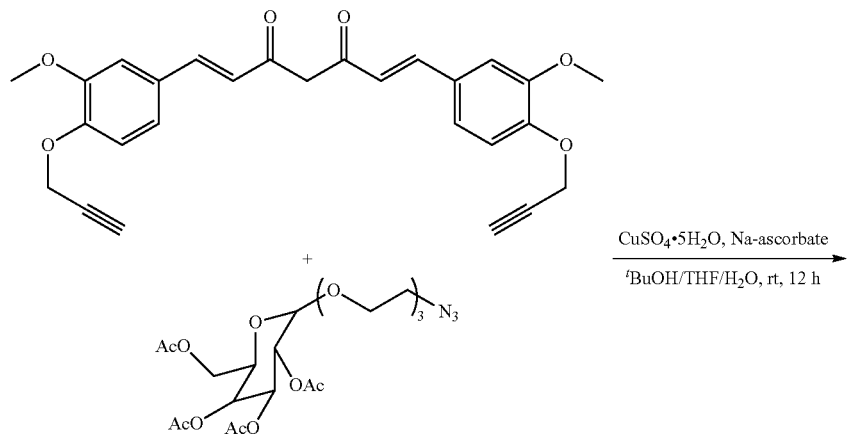

The reaction was stopped and the solvent was removed by evaporation. The crude product was extracted from water-chloroform mixture. The organic layer was dried over anhydrous NaSO$_4$ and solvent was evaporated. Finally the product was purified via column chromatography using Chloroform:Ethyl acetate (90:10) mixture to yield orange solid. Yield: 978 mg (60%). $^1$H NMR (CDCl$_3$, 600 MHz): δ (ppm) 1.93 (s, 6H), 1.97-1.98 (d, 12H), 2.08 (s, 6H), 3.50-3.56 (m, 12H), 3.64-3.65 (m, 2H), 3.81-3.90 (m, 14H), 4.04-4.12 (m, 6H), 4.46-4.50 (m, 6H), 4.94-4.97 (dd, 2H),

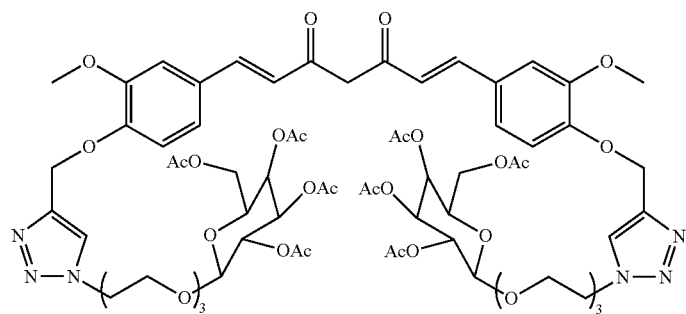

Curcumin di-alkyne (2a) (500 mg, 1.12 mmol) was dissolved in 2 mL of THF and added to 2 mL of t-BuOH containing commercially available acetal-protected Azido-Galactose derivative [2-[2-(2-Azidoethoxy)ethoxy]ethyl-2,3,4,6-Tetra-O-acetyl-D-galactopyranoside] (1.14 g, 2.25 mmol) in a round bottom flask (r.b.). Fresh solutions of CuSO$_4$.5H$_2$O (100 mg, 0.4 mmol) and Sodium Ascorbate (90 mg, 0.45 mmol) were prepared separately in 1 mL of milipore water. Sodium Ascorbate solution was added to the r.b. followed by CuSO$_4$ solution and stirred for 12 hours.

5.12-5.15 (m, 2H), 5.25-5.28 (m, 4H), 5.32 (d, 2H), 5.77 (s, 1H), 6.43-6.46 (d, 2H), 7.02-7.06 (m, 4H), 7.52-7.54 (d, 2H), 7.80 (s, 2H); $^{13}$C NMR (CDCl$_3$, 150 MHz): δ (ppm): 20.57, 20.63, 20.65, 20.73, 50.32, 55.92, 61.17, 62.89, 66.99, 68.77, 69.11, 69.37, 70.17, 70.54, 70.56, 70.62, 70.82, 101.31, 110.38, 113.66, 122.30, 122.34, 124.30, 128.70, 140.23, 143.49, 149.61, 149.62, 169.40, 170.12, 170.21, 170.36, 183.17; ESI-MS: for C$_{67}$H$_{86}$N$_6$O$_{30}$; calculated-1454.54; observed-1455.2 [M+H]$^+$, 738.3 [M+Na]$^{2+}$.

6. Synthesis of Curcumin 'Clicked' di-galactose

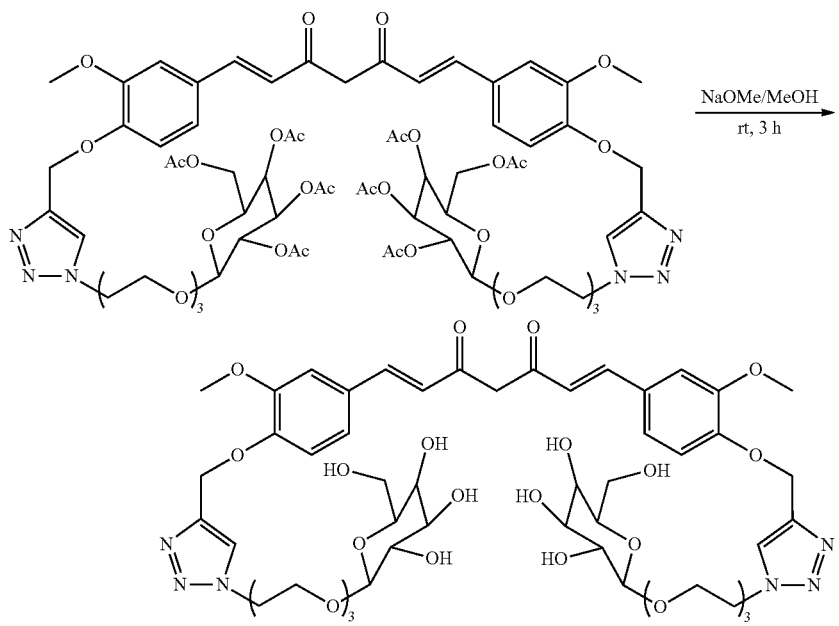

Protected curcumin-"clicked"-di-galactose (100 mg, 0.069 mmol) was dissolved in 3 mL of 0.3 M NaOMe in anhydrous MeOH. The mixture was stirred for 3 hours at room temperature. The pH of the solution was neutralized to pH=7 using Amberlite15 ion exchange resin and the color of the solution became light yellow from dark orange. The solution was filtered and the solvent was removed. Finally the crude product was purified via column chromatography using $CHCl_3$:MeOH (95:5) to yield 1c as a dark yellow-orange solid. Yield: 66 mg (85%). $^1$H NMR ($CD_3OD$, 600 MHz): δ (ppm) 3.52 (s, 4H), 2.65 (s, 4H), 3.01 (s, 1H), 3.09-3.13 (m, 4H), 3.17-3.22 (m, 2H), 3.25-3.29 (m, 12H), 3.26-3,41 (m, 6H), 3.46-3.51 (m, 2H), 3.53-3.56 (m, 6H), 3.62-3.63 (m, 2H), 3.85-3.87 (d, 2H), 4.26-4.50 (t, 4H), 4.91 (s, 2H), 6.33-6.36 (d, 2H), 6.78-6.91 (m, 4H), 7.57-7.59 (d, 2H), 7.64 (s, 1H), 7.80 (s, 2H); $^{13}$C NMR ($CDCl_3$, 150 MHz): δ (ppm) 30.22, 35.52, 49.72, 55.12, 61.12, 61.93, 68.17, 68.86, 69.97, 71.08, 73.47, 75.25, 103.63, 110.66, 113.97, 114.52, 122.24, 125.16, 129.02, 140.23, 143.04, 149.72, 149.98, 163.43. ESI-MS: for $C_{51}H_{70}N_6O_{22}$; calculated-1118.45; observed-1119.4 $[M+H]^+$, 560.4 $[M+2H]^{2+}$.

7. Synthesis of Curcumin mono-carboxylic acid (1b)

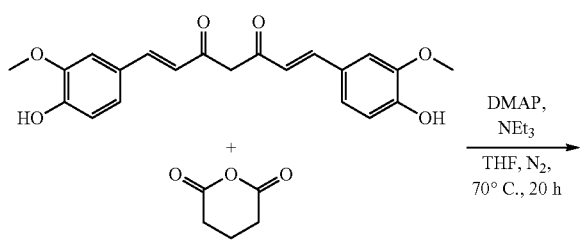

To a solution of 2.01 g (5.46 mmol) of curcumin 1, and 112 mg (0.92 mmol) of DMAP in 100 ml THF was added 1.33 ml (9.55 mmol) of $Et_3N$. 0.685 g (6 mmol) of glutaric anhydride (95%) in 5 mL THF was added slowly dropwise to the curcumin solution. The mixture was stirred and refluxed under argon overnight. THF was removed under vacuum, 55 mL EtOAc was added, followed by the addition of 15 mL of 1M HCL, the mixture was stirred for 10 minutes. The organic phase was separated and extracted with EtOAc three times; the solvent was removed and dried. The product was purified via column chromatography, eluting with $CH_2Cl_2$:MeOH, 95:5. Yield: 69%. $^1$HNMR ($CDCl_3$), δ (ppm): 2.10-2.12 (t, 2H); 2.56-2.58 (t, 2H); 2.69-2.72 (t, 2H); 3.87 (s, 3H); 3.94 (s, 3H); 5.83 (s, 2H); 6.48-6.57 (t, 2H); 6.48-6.57 (m, 1H); 6.94-7.16 (m, 5H); 7.59-7.62 (d, 2H). $^{13}$C NMR ($CDCl_3$), δ (ppm): 19.87; 32.65; 55.70; 101.48; 109.73; 111.23; 114.91; 120.83; 121.42; 123.02; 124.03; 127.22; 133.76; 133.90; 139.25; 141.06; 146.89; 148.09; 151.09; 170.85; 177.24; 181.59; 184.51. MS (ESI) calcd. for $C_{26}H_{26}O_9$: 482.48; found: 483.2 $[M+H]^+$.

8. Synthesis of curcumin mono-1,2:3,4-di-O-isopropylidene-D-galactopyranose ester

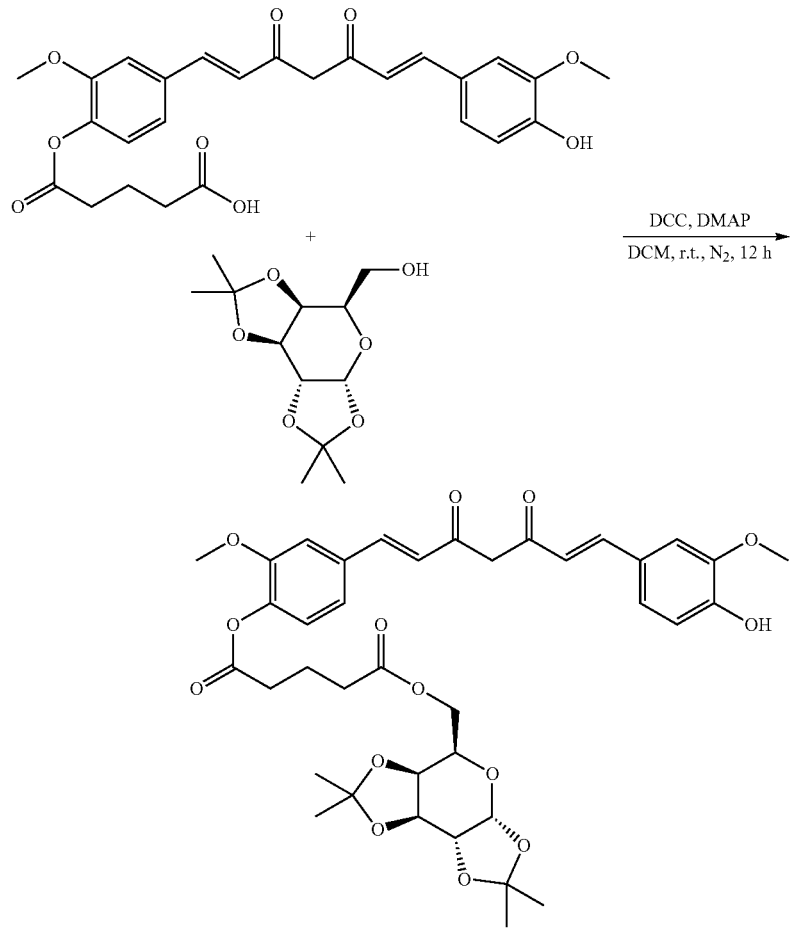

Curcumin mono-carboxylic acid (1 g, 2.07 mmol), 1,2:3, 4-Di-O-isopropylidene-D-galactopyranose (97%) (535 mg, 2.05 mmol) and 4-Dimethylaminopyridine (12.5 mg, 0.10 mmol) were dissolved in 10 mL dry DCM and cooled to 0° C. 1,3-Dicyclohexylcarbodiimide (640 mg, 3.10 mmol) in 5 mL dry DCM was added drop-wise to the reaction mixture while stirring. Formed Dicyclohexyl urea was filtered off after stirring the reaction mixture at room temperature under $N_2$ atmosphere for 12 hrs. The crude product was finally purified via column chromatography using CHCl3:EtOAc (95:5) as eluent. The product was isolated as orange powder. Yield: 1.195 g (80%). $^1$HNMR (600 MHz, CDCl$_3$), δ (ppm): 1.17-1.33 (m); 1.45 (s); 1.50 (s); 1.52 (s); 1.54-1.57 (m); 1.67-1.74 (m); 1.90-1.91 (m); 2.20-2.24 (p); 2.51-2.54 (t); 2.66-2.68 (t); 2.76-2.79 (t); 3.17-3.20 (m); 3.46-3.48 (m); 3.71-3.76 (m); 3.83 (s); 3.84 (s); 3.87 (s); 3.92 (s), 4.26-4.27 (d); 4.32-4.33 (m); 4.60-4.61 (d); 5.55-5.56 (d); 5.82-5.85 (m); 6.54-6.57 (d); 6.90-6.91 (d); 7.03-7.14 (m); 7.59-7.62 (d). MS (ESI) calcd. for $C_{38}H_{44}O_{14}$: 724.27; found: 725.25 $[M+H]^+$.

9. Synthesis of Curcumin di-carboxylic acid (2b)

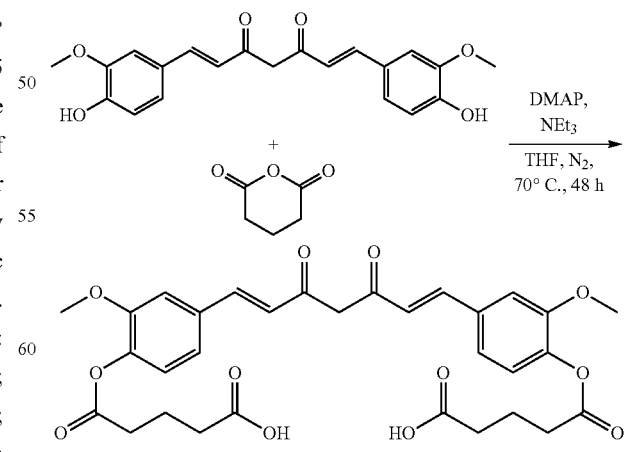

To a solution of 4 g (10.86 mmol) of curcumin, and 330 mg (2.71 mmol) of DMAP in 140 ml THF was added 3.78 ml (27.15 mmol) of Et$_3$N. 2.73 g (23.88 mmol) of glutaric anhydride (95%) in 10 mL THF was added slowly dropwise to the curcumin solution. The mixture was stirred and refluxed under N$_2$ atmosphere for 48 hrs. THF was removed under vacuum, redissolved in 100 mL CHCl$_3$ and washed with 100 mL 0.1 N HCl followed by water (3×50 mL) and brine (3×50 mL). The organic layer was separated and dried over anhydrous Na$_2$SO$_4$. The product was purified via column chromatography, eluting with CHCl$_3$:EtOAc (95:5) and isolated as dark yellow powder. Yield: 69%. $^1$HNMR (600 MHz, CDCl$_3$), δ (ppm): 2.07-2.10 (t, 4H); 2.53-2.55 (t, 4H); 2.67-2.69 (t, 4H); 3.84 (s, 6H); 5.82 (s, 2H); 6.51-6.54 (d, 2H); 7.02-7.13 (m, 6H); 7.57-7.59 (d, 2H). $^{13}$C NMR (150 MHz, CDCl$_3$), δ (ppm): 19.87; 32.65; 55.70; 101.48; 109.73; 111.23; 114.91; 120.83; 121.42; 123.02; 124.03; 127.22; 133.76; 133.90; 139.25; 141.06; 146.89; 148.09; 151.09; 170.85; 177.24; 181.59; 184.51. MS (ESI) calcd. for C$_{31}$H$_{32}$O$_{12}$: 596.19; found: 597.20 [M+H]$^+$.

Curcumin mono-carboxylic acid (1 g, 1.67 mmol), 1,2:3,4-Di-O-isopropylidene-D-galactopyranose (97%) (690 mg, 2.65 mmol) and 4-Dimethylaminopyridine (12.5 mg, 0.10 mmol) were dissolved in 10 mL dry DCM and cooled to 0° C. 1,3-Dicyclohexylcarbodiimide (860 mg, 4.16 mmol) in 5 mL dry DCM was added drop-wise to the reaction mixture while stirring. Formed di-cyclohexyl urea was filtered off after stirring the reaction mixture at room temperature under N$_2$ atmosphere for 12 hrs. The crude product was finally purified via column chromatography using CHCl$_3$:EtOAc (95:5) as eluent. The product was isolated as dark orange powder. Yield: 1.31 g (72%). $^1$HNMR (600 MHz, CDCl$_3$), δ (ppm): 1.15-1.34 (m); 1.43 (s); 1.48 (s); 1.50 (s); 1.52-1.55 (m); 1.69-1.71 (m); 1.88-1.89 (m); 2.04-2.09 (p); 2.18-2.23 (p); 2.38-2.40 (t); 2.49-2.52 (t); 2.64-2.66 (t); 2.75-2.77 (t); 3.14-3.19 (m); 3.84-3.85 (d); 4.17-4.32 (m); 4.57-4.60 (m); 5.11-5.12 (d); 5.83 (s); 5.52-6.55 (dd); 7.02-7.14 (m); 7.57-7.60 (dd). $^{13}$C NMR (150 MHz, CDCl$_3$), δ (ppm): 14.22; 20.26; 24.49; 24.97; 25.98; 26.01; 33.01; 33.98; 34.94; 55.90; 60.40; 63.53; 65.98; 70.44; 70.72; 71.07; 96.32; 108.78; 109.67: 121.08: 122.15: 123.25: 124.24; 129.24; 133.92; 139.98; 141.33; 151.37; 170.82; 172.80; 183.10. MS (ESI) calcd. for C$_{55}$H$_{68}$O$_{22}$: 1080.42; found: 1081.40 [M+H]$^+$.

10. Synthesis of curcumin di-1,2:3,4-di-O-isopropylidene-D-galactopyranose ester

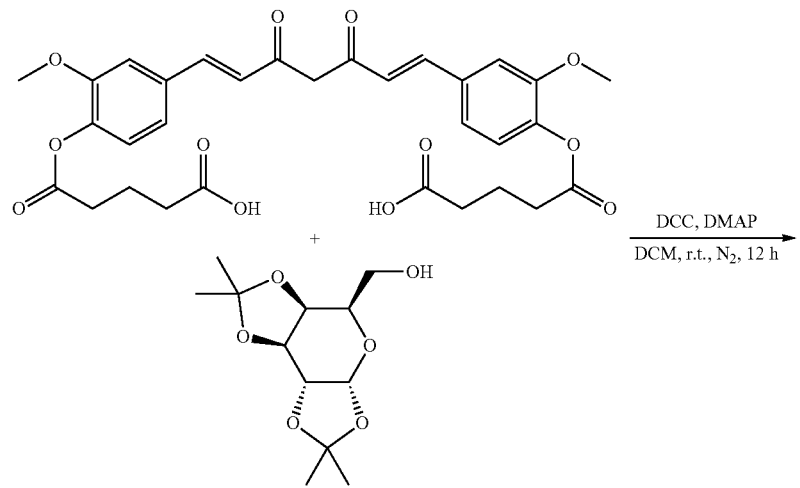

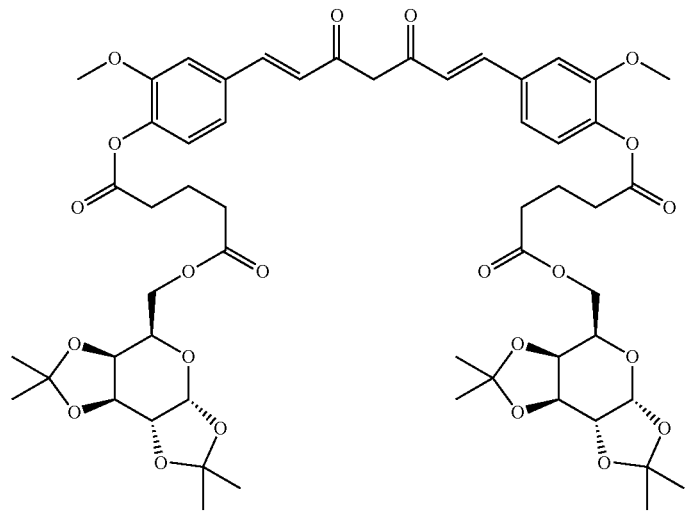

11. Solubility and Anti-Oxidant Activity Study of Curcumin mono-galactose (Sweet Curry) 1d a. Solubility Study Via UV-Vis Spectroscopy.

The improved solubility of the curcumin sugar conjugate 1d was confirmed by UV spectroscopy via the following procedure: 5 mg of curcumin-sugar conjugate 1d was vortexed in 1 ml of deionized water in an eppendorf™ tube to create a stock solution of 5 mg/ml. A control sample was also prepared by adding 5 mg of curcumin in 1 ml of water in an eppendorf™ tube and vortexed. Both sample were centrifuged at 13,000 RPM for 2 min. 100 μL of the sugar conjugate solution was added to 900 μL of deionized water and thoroughly mixed. The UV-vis absorbance of the diluted sugar-curcumin conjugate and the stock curcumin solution were recorded. It is evident from the UV spectra that the conjugate 1d (6 mM in water, calculated from a previously determined molar extinction coefficient) has vastly improved solubility relative to curcumin (0.0 mM in water). It should be noted that the solubility study outlined above measures the direct solubility of the compounds in water and closely models "real life" conditions, in contrast to other experiments in which the compounds are first dissolved in other solvents followed by dilution in water. Sweet curry 1d thus has a far superior solubility compared to curcumin in water (plasma model).

b. Antioxidant Potentiality Assay by Linoleic Acid Peroxidation Method:

Using the Thiocyanide method, antioxdant potentiality assay was carried out with Curcumin 1, curcumin mono-alkyne 1a, curcumin mono-carboxylic acid 1b and sweet curry 1d (curcumin mono-galactose). 0.28 gm of linoleic acid, 0.28 gm of tween 40 as emulsifier and 50 ml of phosphate buffer (0.2 M, pH 7) were used to prepare a linoleic acid emulsion. The curcuminoids (5 mg per ml) were dissolved in water and 0.5 ml of each one of them was pipetted out into different test-tubes. Then 2.5 ml of linoleic acid emulsion was added to each one of them followed by the addition of 2.5 ml of phosphate buffer. All the tubes were incubated at 37° C. for 7 days. The mixture prepared as above without test sample was the control one. At the regular interval of 24 hours, 0.1 ml of the aliquots were drawn out of the incubation mixture and mixed with 5 ml of 75% ethanol, 0.1 ml of 30% ammonium thiocyanate and 0.1 ml of 20 mM ferrous chloride in 3.5% HCl. The tubes were allowed to stand in room temperature for 3 minutes. Spectrophotometric analysis was done at 500 nm. All the tests were carried out in duplicate and averaged.

Anoxidant activity=[1-increase in absorbance of the sample/increase in absorbance of control]*100.

12. Cell Viability Assay to Assess the Effect of Sweet Curry on Normal Brain Cells Using MTT To assess the viability of the normal brain tissue in presence of the sweet curry MTT assay on cultured hippocampal slices were performed.

The results of the MTT assay show that at low concentrations (i.e. 8 nM and 8 μM) the viability of the cells is near the control samples but at a higher concentration (i.e., 80 μM) cell viability was a little higher than the control samples, which shows that the sweet curry has no harmful effect on the normal brain tissue as long as viability is concerned. Hence, the sweet curry has no harmful effect upon normal brain cells at low concentrations, and at higher concentrations the cell viability among the brain cells is even better.

a. Hippocampal Slice Culture[25]:

Mouse pups of specific ages were anesthetized with ketamine (100 mg/kg) and decapitated. Under sterile conditions, the brains were isolated and then cut at 60° from the longitudinal fissure at the top using a hippocampus-dissecting tool to expose the hippocampus. The hemispheres containing the hippocampi were then placed in modified Gey's balanced salt solution (mGBSS) at 4° C. for 30-40 minutes while bubbling a mixture of 95% $O_2$ and 5% $CO_2$. Individual hippocampi were isolated using dissection tool and then 400 μM thick transverse slices were prepared using a tissue chopper (Stoelting, Wood Dale, Ill., USA). The slices were placed in ice cold mGBSS and inspected using a dissection microscope for the presence of uninterrupted bright transparent neuronal layers characteristic of the hippocampal structure. Only such slices were placed on Millicell CM filters (Millipore, Bedford, Mass., USA). The filters were placed in a six well dish with 1 ml of medium in each well. The slices were kept on high $K^+$ culture medium (25% horse serum, 50% Basal Essential Media-Eagles, 25% Eagle's Balanced Salt Solution (EBSS), 25 mM Na-HEPES, 1 mM Glutamine, 28 mM Glucose, pH 7.2) for the first two days. After incubation at 32° C. in a 5% $CO_2$ atmosphere, the culture medium was changed to physiological $K^+$ slice culture medium (20% dialyzed fetal bovine serum, 5% Basal Essential Media-Eagles, and EBSS modified to adjust the $K^+$ concentration to 2.66 mM). After 20% dialyzed serum treatment for two days and the slices were placed in 5% serum medium (same medium as above but with 5% serum) for two days.

b. MTT Assay: MTT Assay Was Done According to the Protocol Described by Purkayastha et al[26]

Hippocampal slices from adult mice brain were cultured as described by Mehta et al (2007). After six days in vitro the slices were treated with different concentrations of the sweet curry (i.e., 8 nM, 8 μM and 80 μM respectively) overnight along with the slices treated with the carrier as control.

After the treatment with sweet curry, slices from each treatment group were placed in 400 μl PBS in one well of 48-well plate and then treated with 200 μl of MTT (5 mg/ml) per well with gentle mixing at 37° C. for 2 hours. The slices were triturated to homogenize with the help of a micropipette. After that 800 μl of lysis buffer (20% SDS, 50% dimethylformamide) was added to each well and the plate was sealed and incubated overnight at 37° C. with gentle mixing. Now 100 μl mix from each well was taken in respective wells of a 96 well plate in triplicates and absorbance was measured at 570 nm using a plate reader. Results obtained were normalized to the total protein content and then expressed as percent carrier-treated samples.

13. Dissolution of Amyloid βeta (Aβeta) Fragments

Amyloid βeta (Aβeta) fragment 25-35 (Sigma A-4559) was diluted in water to a stock of 1 mg/ml. 10 μM curcumin and sweet curry stocks were also prepared in distilled water. Samples were prepared so that an equal volume of Aβeta and the appropriate curcumin (sweet curry or curcumin) were added in a 1:1 ratio so that the final concentration of the Aβeta was 50 μg/ml and the curry was diluted to the desired molar concentration. Samples were incubated at 37° C. for 6 days. Aggregation of the protein fragment was determined using transmission electron microscopy. 200 mesh carbon coated grids (Electron Microscopy Sciences) were used and prepared for negative staining by adding 5 µl of incubation mixture to the grid surface for one minute, followed by drying the grid with filter paper and contrasting with 5 µl of freshly filtered 2% phosphotungstic acid (pH=7.2) for one minute. Once grids were dry, examination was done using the FEI Tecnai Spirit at the College of Staten Island's Advanced Imaging Facility. Micrographs were captured using an AMT CCD camera.

The electron micrographs demonstrate that sweet curry (1d) is significantly more effective than curcumin in dissolving amyloid aggregates. From the series of micrographs 1d works at 8 nmol compared to 8 micromolar for curcumin (1000 times more effective) This can correlated with its superior water solublity.

REFERENCES CITED

1. Roberson, E. D.; Scearce-Levie, K.; Palop, J. J.; Yan, F.; Cheng, I. H.; Wu, T.; Gerstein, H.; Yu, G. Q.; Mucke, L., Reducing endogenous tau ameliorates amyloid beta-induced deficits in an Alzheimer's disease mouse model. *Science* 2007, 316 (5825), 750-4.
2. Chattopadhyay, I.; Biswas, K.; Bandyopadhyay, U.; Banerjee, R. K., Turmeric and curcumin: Biological actions and medicinal applications. *Current Science* 2004, 87 (1), 44-53
3. Goel, A.; Kunnumakkara, A. B.; Aggarwal, B. B., Curcumin as "Curecumin": from kitchen to clinic. *Biochem Pharmacol* 2008, 75 (4), 787-809.
4. Hatcher, H.; Planalp, R.; Cho, J.; Torti, F. M.; Torti, S. V., Curcumin: from ancient medicine to current clinical trials. *Cell Mol Life Sci* 2008, 65 (11), 1631-52.
5. Aggarwal, B. B.; Shishodia, S., Molecular targets of dietary agents for prevention and therapy of cancer. *Biochem Pharmacol* 2006, 71 (10), 1397-421.
6. Leyon, P. V.; Kuttan, G., Studies on the role of some synthetic curcuminoid derivatives in the inhibition of tumour specific angiogenesis. *J Exp Clin Cancer Res* 2003, 22 (1), 77-83.
7. Nurfinal, A. N.; Reksohadiprodjo, M. S.; Timmerman, H.; Jenie, U. A.; Sugiyant, D.; van der Goot, H., Synthesis of some symmetrical curcumin derivatives and their anti inflammatory activity. *European Journal of Medicinal Chemistry* 1997, 32 (4), 321-328.
8. Cole, G. M.; Teter, B.; Frautschy, S. A., Neuroprotective effects of curcumin. *Adv Exp Med Biol* 2007, 595, 197-212.
9. Strimpakos, A. S.; Sharma, R. A., Curcumin: preventive and therapeutic properties in laboratory studies and clinical trials. *Antioxid Redox Signal* 2008, 10 (3), 511-45.
10. Lim, G. P.; Chu, T.; Yang, F.; Beech, W.; Frautschy, S. A.; Cole, G. M., The curry spice curcumin reduces oxidative damage and amyloid pathology in an Alzheimer transgenic mouse. *J Neurosci* 2001, 21 (21), 8370-7.
11. Yang, F.; Lim, G. P.; Begum, A. N.; Ubeda, O. J.; Simmons, M. R.; Ambegaokar, S. S.; Chen, P. P.; Kayed, R.; Glabe, C. G.; Frautschy, S. A.; Cole, G. M., Curcumin inhibits formation of amyloid beta oligomers and fibrils, binds plaques, and reduces amyloid in vivo. *J Biol Chem* 2005, 280 (7), 5892-901.
12. Ringman, J. M.; Frautschy, S. A.; Cole, G. M.; Masterman, D. L.; Cummings, J. L., A potential role of the curry spice curcumin in Alzheimer's disease. *Curr Alzheimer Res* 2005, 2 (2), 131-6.
13. Garcia-Alloza, M.; Borrelli, L. A.; Rozkalne, A.; Hyman, B. T.; Bacskai, B. J., Curcumin labels amyloid pathology in vivo, disrupts existing plaques, and partially restores distorted neurites in an Alzheimer mouse model. *J Neurochem* 2007, 102 (4), 1095-104.
14. Ma, Q. L.; Yang, F.; Calon, F.; Ubeda, O. J.; Hansen, J. E.; Weisbart, R. H.; Beech, W.; Frautschy, S. A.; Cole, G. M., p21-activated kinase-aberrant activation and translocation in Alzheimer disease pathogenesis. *J Biol Chem* 2008, 283 (20), 14132-43.
15. Fiala, M.; Liu, P. T.; Espinosa-Jeffrey, A.; Rosenthal, M. J.; Bernard, G.; Ringman, J. M.; Sayre, J.; Zhang, L.; Zaghi, J.; Dejbakhsh, S.; Chiang, B.; Hui, J.; Mahanian, M.; Baghaee, A.; Hong, P.; Cashman, J., Innate immunity and transcription of MGAT-III and Toll-like receptors in Alzheimer's disease patients are improved by bisdemethoxycurcumin. *Proc Natl Acad Sci USA* 2007, 104 (31), 12849-54.
16. Yang, S.; Zhang, D.; Yang, Z.; Hu, X.; Qian, S.; Liu, J.; Wilson, B.; Block, M.; Hong, J. S., Curcumin protects dopaminergic neuron against LPS induced neurotoxicity in primary rat neuron/glia culture. *Neurochem Res* 2008, 33 (10), 2044-53.
17. Kim, S. J.; Son, T. G.; Park, H. R.; Park, M.; Kim, M. S.; Kim, H. S.; Chung, H. Y.; Mattson, M. P.; Lee, J., Curcumin stimulates proliferation of embryonic neural progenitor cells and neurogenesis in the adult hippocampus. *J Biol Chem* 2008, 283 (21), 14497-505.
18. Narlawar, R.; Pickhardt, M.; Leuchtenberger, S.; Baumann, K.; Krause, S.; Dyrks, T.; Weggen, S.; Mandelkow, E.; Schmidt, B., Curcumin-derived pyrazoles and isoxazoles: Swiss army knives or blunt tools for Alzheimer's disease? *Chem Med Chem* 2008, 3 (1), 165-72.
19. Cheng, A. L.; Hsu, C. H.; Lin, J. K.; Hsu, M. M.; Ho, Y. F.; Shen, T. S.; Ko, J. Y.; Lin, J. T.; Lin, B. R.; Ming-Shiang, W.; Yu, H. S.; Jee, S. H.; Chen, G. S.; Chen, T. M.; Chen, C. A.; Lai, M. K.; Pu, Y. S.; Pan, M. H.; Wang, Y. J.; Tsai, C. C.; Hsieh, C. Y., Phase I clinical trial of curcumin, a chemopreventive agent, in patients with high-risk or pre-malignant lesions. *Anticancer Res* 2001, 21 (4B), 2895-900.
20. Anand, P.; Kunnumakkara, A. B.; Newman, R. A.; Aggarwal, B. B., Bioavailability of curcumin: problems and promises. *Mol Pharm* 2007, 4 (6), 807-18.
21. Shi, W.; Dolai, S.; Rizk, S.; Hussain, A.; Tariq, H.; Averick, S.; L'Amoreaux, W.; El Idrissi, A.; Banerjee, P.; Raja, K., Synthesis of monofunctional curcumin derivatives, clicked curcumin dimer, and a PAMAM dendrimer curcumin conjugate for therapeutic applications. *Org Lett* 2007, 9 (26), 5461-4.
22. Ryu, E. K.; Choe, Y. S.; Lee, K. H.; Choi, Y.; Kim, B. T., Curcumin and dehydrozingerone derivatives: synthesis, radiolabeling, and evaluation for beta-amyloid plaque imaging. *J Med Chem* 2006, 49 (20), 6111-9.
23. Pfeiffer, E.; Hoehle, S. I.; Walch, S. G.; Riess, A.; Solyom, A. M.; Metzler, M., Curcuminoids form reactive glucuronides in vitro. *J Agric Food Chem* 2007, 55 (2), 538-44.
24. Pardridge, W. M.; Boado, R. J.; Farrell, C. R., Brain-type glucose transporter (GLUT-1) is selectively localized to the blood-brain barrier. Studies with quantitative western blotting and in situ hybridization. *J Biol Chem* 1990, 265 (29), 18035-40.
25. Mehta, M.; Ahmed, Z.; Fernando, S. S.; Cano-Sanchez, P.; Adayev, T.; Ziemnicka, D.; Wieraszko, A.; Banerjee, P., Plasticity of 5-HT 1A receptor-mediated signaling during early postnatal brain development. *J Neurochem* 2007, 101 (4), 918-28.
26. Purkayastha, S.; Berliner, A.; Fernando, S. S.; Ranasinghe, B.; Ray, I.; Tariq, H.; Banerjee, P., Curcumin Blocks Brain Tumor Formation. *Brain Res* 2009.

The invention claimed is:

1. A curcumin derivative having the formula I:

![Formula I structure showing H3CO-phenyl-A-C(O)-CH2-C(O)-A-phenyl-OCH3 with OR1 and OR2 substituents]

wherein:
A is —$CH_2$—$CH_2$— or —CH═CH—;
$R^1$ represents $L^1_{m1}$-$Y^1$;
$R^2$ represents $L^2_{m2}$-$Y^2$;
$L^1$ and $L^2$ are ![Linker structure showing CH2-triazole-N-(CH2CH2O)n1]

m1 and m2 are 1;
n1 is independently 0 or an integer from 1 to 50;
$Y^1$ and $Y^2$ independently represent a saccharide with 1 to 51 monosaccharide units; $CH_2$—CH═$CH_2$ or $CH_2$—C≡CH;
$R^3$ independently represents a saturated, unbranched hydrocarbyl with 1 to 4 carbon atoms and n2 independently represents an integer from 5 and 50.

2. A curcumin derivative according to claim 1, wherein $L^1$ is

![Linker structure]

and $Y^1$ is a saccharide.

3. A curcumin derivative according to claim 2, wherein the saccharide is a monosaccharide.

4. A curcumin derivative according to claim 3, wherein the monosaccharide is glucose or galactose.

5. A curcumin derivative according to claim 1, wherein $Y^1$ or $Y^2$ is a saccharide.

6. A curcumin derivative according to claim 1, wherein $Y^1$ or $Y^2$ is a disaccharide or a trisaccharide.

7. A curcumin derivative according to claim 1, wherein the saccharide is a monosaccharide.

8. A curcumin derivative according to claim 1, wherein the monosaccharide is glucose or galactose.

9. A method of treating Alzheimer's disease in a patient comprising administering to the patient in need thereof a therapeutically effective amount of a curcumin derivative having the formula I:

![Formula I structure showing H3CO-phenyl-A-C(O)-CH2-C(O)-A-phenyl-OCH3 with OR1 and OR2 substituents]

wherein:
A is —$CH_2$—$CH_2$— or —CH═CH—;
$R^1$ represents $L^1_{m1}$-$Y^1$;
$R^2$ represents $L^2_{m2}$-$Y^2$;
$L^1$ and $L^2$ are ![Linker structure showing CH2-triazole-N-(CH2CH2O)n1]

m1 and m2 are 1;
n1 is independently 0 or an integer from 1 to 50;
$Y^1$ and $Y^2$ independently represent a saccharide with 1 to 51 monosaccharide units; $CH_2$—CH═$CH_2$ or $CH_2$—C≡CH;
$R^3$ independently represents a saturated, unbranched hydrocarbyl with 1 to 4 carbon atoms; and n2 independently represents an integer from 5 and 50.

* * * * *

UNITED STATES PATENT AND TRADEMARK OFFICE
CERTIFICATE OF CORRECTION

PATENT NO. : 9,650,404 B2  
APPLICATION NO. : 13/581020  
DATED : May 16, 2017  
INVENTOR(S) : Krishnaswami Raja et al.

Page 1 of 1

It is certified that error appears in the above-identified patent and that said Letters Patent is hereby corrected as shown below:

In the Specification

Column 35, Lines 33 and 34:  
Now reads: "…0.28 gm…"  
Should read: -- …0.28 mg… --

Signed and Sealed this  
Nineteenth Day of September, 2017

Joseph Matal  
*Performing the Functions and Duties of the*  
*Under Secretary of Commerce for Intellectual Property and*  
*Director of the United States Patent and Trademark Office*